United States Patent [19]
Danko

[11] Patent Number: 5,805,278
[45] Date of Patent: *Sep. 8, 1998

[54] PARTICLE DETECTION METHOD AND APPARATUS

[75] Inventor: Joseph J. Danko, Franklin, Mass.

[73] Assignee: Inspex, Inc., Billerica, Mass.

[*] Notice: The term of this patent shall not extend beyond the expiration date of Pat. No. 5,659,390.

[21] Appl. No.: 668,494

[22] Filed: Jun. 18, 1996

Related U.S. Application Data

[63] Continuation-in-part of Ser. No. 386,289, Feb. 9, 1995.
[51] Int. Cl.$^6$ .................................................. G01N 21/00
[52] U.S. Cl. ...................... 356/237; 356/376; 250/559.41
[58] Field of Search ..................................... 356/237, 376; 250/559.41

[56] References Cited

U.S. PATENT DOCUMENTS

| | | |
|---|---|---|
| 4,000,949 | 1/1977 | Watkins . |
| 4,806,774 | 2/1989 | Lin et al. . |
| 4,889,998 | 12/1989 | Hayano et al. . |
| 5,046,847 | 9/1991 | Nakata et al. . |
| 5,090,807 | 2/1992 | Tai . |
| 5,276,498 | 1/1994 | Galbraith et al. . |
| 5,659,390 | 8/1997 | Danko ..................................... 356/237 |

OTHER PUBLICATIONS

Hamamatsu Photonics K.K., Hamamatsu Technical Data, Ferroelectric Liquid Crystal Spatial Light Modulator (FLC–SLM) model X4601, 4 pages.

Hamamatsu Photonics K.K., Hamamatsu Technical Data, Parallel Aligned Nematic Liquid Crystal Spatial Light Modulator (PAL–SLM) model X5641.

*Primary Examiner*—Frank G. Font
*Assistant Examiner*—Reginald A. Ratliff
*Attorney, Agent, or Firm*—Kriegsman & Kriegsman

[57] ABSTRACT

An apparatus and method for detecting particles on a surface of a semiconductor wafer having repetitive patterns includes a laser for illuminating an area on the front surface at grazing angle of incidence with a beam of polarized light. A lens collects light scattered from the area and forms a Fourier diffraction pattern of the area illuminated. A Fourier mask blocks out light collected by the lens at locations in the Fourier diffraction pattern where the intensity is above a predetermined level indicative of background information and leaves in light at locations where the intensity is below the threshold level indicative of possible particle information. The Fourier mask includes an optically addressable spatial light modulator and a polarization discriminator. A camera detects scattered light collected from the area by the lens and not blocked out by the Fourier mask.

22 Claims, 6 Drawing Sheets

PARTICLE DETECTION METHOD AND APPARATUS

CROSS-REFERENCE TO RELATED APPLICATIONS

This application is a continuation-in-part of U.S. patent application Ser. No. 08/386,289 filed on Feb. 9, 1995 and assigned to the assignee of this application.

BACKGROUND OF THE INVENTION

The present invention relates generally to a method and apparatus for detecting the presence of particles on the surface of an object and more particularly to a method and apparatus for detecting contaminant particles on a surface of a semiconductor wafer using the principle of light scattering, the surface having repetitive patterns. An example of a semiconductor wafer having a surface containing repetitive patterns is a memory wafer.

There are a variety of existing ways for detecting and measuring the number and sizes of particles on the surface of a semiconductor wafer for the purpose of rejecting those wafers which have on their surface one or more particles above certain sizes or an excessive number of particles. One of the more simple methods involves having a human operator inspect the wafer using a light field/dark field microscope. Using the eye, the operator actually counts the number of particles and also identifies the size of the particles, such as those between 1 and 20 microns, and then rejects those wafers which have particles of or above a certain size or which have an excessive number of particles. This method, however, is highly inaccurate and very expensive both in terms of wages for the human operator and in terms of the number of rejects both after the inspection and after production of the chips (when an erroneously passed wafer is found to have an electrical defect, e.g., short circuits, because of the presence of contaminant particles).

In U.S. Pat. No. 5,317,380, issued May 31, 1994, and assigned to Inspex, Inc. there is disclosed a method and apparatus for detecting particles on a surface of an object, such as a virgin or patterned semiconductor wafer, ceramic tile, or the like. In one embodiment, an apparatus is provided in which a scanning beam of laser light is brought to focus as an arcuate scan line on a surface of the object at a grazing angle of incidence using an off-axis hypertelecentric mirror. A pair of light detectors are positioned at a meridional angle of about 30 degrees and at an azimuthal angle of about 4 degrees to measure forward scattered light from the surface. The object is then moved translationally so that the beam can scan another line of the surface. A light trap is provided to trap light that is reflected by the surface, and a series of masks are provided to mask light which is scattered by the hypertelecentric mirror and in the case of pattered objects, light which is diffracted by the pattern imprinted on the object.

In U.S. Pat. No. 5,046,847, issued on Sep. 10, 1991 and assigned to Hitachi Ltd. there is disclosed a method and apparatus for detecting foreign matter on a sample by illuminating a stripe-shaped region with linearly polarized light. Some of the light reflected by the sample is intercepted by a light intercepting stage, and the rest of the light reflected by the sample, which passes through the light intercepting stage is directed to a detecting optical system, to be detected by a photodetector. The sample is illuminated obliquely at a predetermined angle with respect to a group of straight lines constituting a primary pattern on the sample. The angle is selected so that the diffraction light reflected by the group of straight lines does not enter the detecting optical system. A polarizing spatial filter using a liquid crystal element may be disposed in a predetermined restricted region, in a spacial frequency region, or Fourier transformation plane, within the detecting optical system. The light scattered by the sample may further be separated in the detecting optical system into partial beams having different wave orientation characteristics, which characteristics are detected by a number of one-dimensional solid state imaging elements. The signals are processed by a driver, adder, and quantizer in synchronism with the one-dimensional solid state imaging elements.

In U.S. Pat. No. 4,898,471, issued Feb. 6, 1990, and assigned to Tencor Instruments, a system for detecting particles and other defects on a patterned semiconductor wafer, photomask, or the like is disclosed. The system includes a light source for emitting a beam of light. A polarizing filter is used to polarize the beam of light in a direction substantially parallel to the surface of the patterned semiconductor wafer to be examined. The beam is enlarged in cross-sectional diameter by a beam expander placed along the path of the beam after the polarizing filter. The beam is then caused to scan by a deflection mirror. A telecentric lens brings the scanning beam to focus on the patterned wafer at a shallow angle of incidence, the beam striking the wafer surface substantially parallel to the pattern streets formed on the wafer. A light collection system for detecting side scattered light is positioned in the plane of the scan line. The light collection system, which includes a lens for focusing the side scattered light, a polarizing filter oriented in a direction substantially parallel to the surface of the patterned wafer, and a photomultiplier tube for detecting light incident thereon and transmitting electrical signals in response thereto, receives light scattered in a direction less than 15 degrees above the surface and at angel relative to the beam direction in a range from about 80 degrees to 100 degrees. A processor constructs templates from the electrical signal corresponding to individual patterns and compares the templates to identify particles.

In U.S. Pat. No. 4,806,744 issued Feb. 21, 1989 and assigned to Insystems, Inc., there is disclosed an inspection system which employs a Fourier transform lens and an inverse Fourier transform lens positioned along an optic axis to produce from an illuminated area of a patterned specimen wafer a spatial frequency spectrum whose frequency components can be selectively filtered to produce an image pattern of defects in the illuminated area of the wafer. Depending on the optical components configuration of the inspection system, the filtering can be accomplished by a spatial filter of either the transmissive or reflective type. The lenses collect light diffracted by a wafer die aligned with the optic axis and light diffracted by other wafer dies proximately located to such die. The inspection system is useful for inspecting only dies having many redundant circuit patterns. The filtered image strikes the surface of a two-dimensional photodetector array which detects the presence of light corresponding to defects in only the illuminated on-axis wafer die. Inspection of all possible defects in the portions of the wafer surface having many redundant circuit patterns is accomplished by mounting the wafer onto a two-dimensional translation stage and moving the stage so that the illuminated area continuously scans across the wafer surface from die to die until the desired portions of the wafer surface have been illuminated. The use of a time delay integration technique permits continuous stage movement and inspection of the wafer surface in a raster scan fashion.

In U.S. Pat. No. 4,895,446 to M. C. Maldari et al., there is disclosed a method and apparatus for detecting the presence of particles on the surface of an object such as the front side of a patterned semiconductor wafer. A vertically expanded, horizontally scanning, beam of light is directed onto an area on the surface of the object at grazing angle of incidence. A video camera positioned above the surface detects light scattered from any particles which may be present on the surface, but not specularly reflected light. The surface is angularly repositioned (rotated) relative to the incident light beam so that the diffracted light form the surface and the pattern of lines on the surface is at a minimum. The object is then moved translationally to expose another area to the incident light beam so that the entire surface of the object or selected portions thereof can be examined, one area at a time. The patent also discloses the use of a mark containing a pattern corresponding to the Fourier transform of the patterned surface to mask off light scattered from the pattern on the surface but not any particles that may be present on the surface.

In U.S. Pat. No. 4,377,340 to G. P. Green et al., there is disclosed a method and apparatus for detecting and measuring the number and sizes of impurities on the surface of a material, such as a semiconductor wafer, wherein a beam of high intensity collimated light from a xenon arc lamp is directed onto the surface at normal incidence in the absence of any extraneous light, through a collimating mirror and a pin hole device and where at the particles will scatter the light, and wherein the surface is viewed by a high light sensitive TV camera which is positioned off-axis to pick up scattered light but not specularly reflected light for display on a viewing screen.

In U.S. Pat. No. 4,342,515 to M. Akiba et al., there is disclosed an inspection apparatus for detecting unfavorable foreign matters existent on the surface of an object such as a semiconductor wafer. The apparatus includes a collimated beam generator portion which projects a collimated beam towards the object to be inspected from a side thereof and a mechanism which senses light reflected from the surface of the object, through a polarizer plate. In accordance with the disclosed technique for using the apparatus, the signal-to-noise ratio between a detection signal generated by a pattern of the foreign matter to be detected and a signal generated by a normal pattern of the object surface and sensed as a noise component are said to be enhanced.

In U.S. Pat. No. 3,782,836 to D. F. Fey et al., there is disclosed a surface irregularity analyzing system which includes structure for directing light toward a surface in a direction having a certain angular relationship to the surface. If the light strikes irregularities in the surface it is reflected in a direction having an angular relationship to the surface other than equal and opposite the incident direction. The amount of light reflected from irregularities in the surface is determined, either photographically or photoelectrically using a detector positioned over the surface, to provide an analysis of irregularities in the surface.

In U.S. Pat. No. 2,947,212 to R. C. Woods, there is disclosed a method of detecting surface conditions on a strip of sheet metal having line markings in which light from a light source is directed towards the surface of the sheet metal in a direction generally perpendicular to the line markings. Non-specular reflection in a selected direction which is perpendicular to the lines, and which is preferably between the angle of incidence and the angle of specular reflection, is monitored by a photoelectric cell which is able to detect a surface flaw by variation in the intensity of the reflected light. The light in the incident beam may be polarized and the light in the selected non-specular reflected beam filtered to pass only such polarized light.

SUMMARY OF THE INVENTION

It is an object of the present invention to provide a new and improved method and apparatus for detecting the presence of contaminant particles on a surface of a semiconductor wafer using the principle of scattered light, the surface having repetitive patterns.

It is another object of the present invention to provide a method and apparatus as described above in which background scatter is filtered out in a new and novel manner.

It is a further object of the present invention to provide a method and apparatus as described above which is designed for use in dark field and bright field illumination applications.

Other objects, as well as features and advantages of the present invention, will be set forth in part in the description which follows, and in part will be obvious from the description or may be learned by practice of the invention. The objects, features, and advantages of the invention may be realized and attained by means of the instrumentalities and combinations particularly pointed out in the appended claims.

Apparatus for detecting particles on a surface of a semiconductor wafer having repetitive patterns according to this invention comprises means for illuminating an area on said surface with a beam of polarized light, optical means for collecting light scattered from the area illuminated, the optical means forming a Fourier diffraction pattern of the area illuminated, a Fourier mask for blocking out from the light collected by the optical means areas in the Fourier diffraction pattern whose intensity is above a predetermined level indicative of background information and letting pass through areas in the Fourier diffraction pattern whose intensity is below the threshold level indicative of possible particle information, the Fourier mask being self-programmable and including an optically addressable spatial light modulator (SLM) and a polarization discriminator, and a camera for detecting light scattered from area collected by the optical means and not blocked out by the Fourier mask. The Fourier mask is self-programmable in that it automatically blocks out the more intense portions of the light in the Fourier diffraction pattern. The SLM is optically addressed using light collected by the optical means.

A method for detecting particles on the front surface of a patterned semiconductor wafer having repetitive pattern according to this invention comprises illuminating an area on the front surface with a beam of polarized light, collecting light scattered from the area illuminated and forming a Fourier diffraction pattern of the light scattered from the area illuminated, blocking out from the light collected areas in the Fourier diffraction pattern whose intensity is above a predetermined level indicative of background information and letting pass through areas in the Fourier diffraction pattern whose intensity is below the threshold level indicative of possible particle information, the blocking being achieved using an apparatus including a spatial light modulator and a polarization discriminator, and detecting scattered light collected from the area illuminated and not blocked out.

BRIEF DESCRIPTION OF THE DRAWINGS

In the drawings wherein like reference numerals represent like parts.

DETAILED DESCRIPTION OF PREFERRED EMBODIMENTS

The present invention is directed to a method and apparatus for detecting the presence of contaminant particles on the surface of a semiconductor wafer using the principle of scattered light, the surface having repetitive patterns.

In accordance with the invention, an area on the surface to be examined is illuminated with a beam of polarized light. A lens collects light scattered from the area illuminated, the lens forming a Fourier diffraction pattern of the scattered light. A Fourier mask blocks out light in areas in the Fourier diffraction pattern above a predetermined intensity level indicative of background information on the wafer and does not block out light in areas which is below the predetermined intensity level indicative of possible particles. The unblocked light is then detected by a camera. The procedure is repeated for other areas on the surface.

The Fourier mask is self-programmable and includes a spatial light modulator which is optically addressable and a polarization discriminator. In some embodiments of the invention the polarization discriminator is in the form of a crossed polarizer, while in other embodiments of the invention the polarization discriminator is in the form of a polarizing beamsplitter. The spatial light modulator is optically addressed using scattered light collected by the lens used to form the Fourier diffraction pattern.

Figure 1:
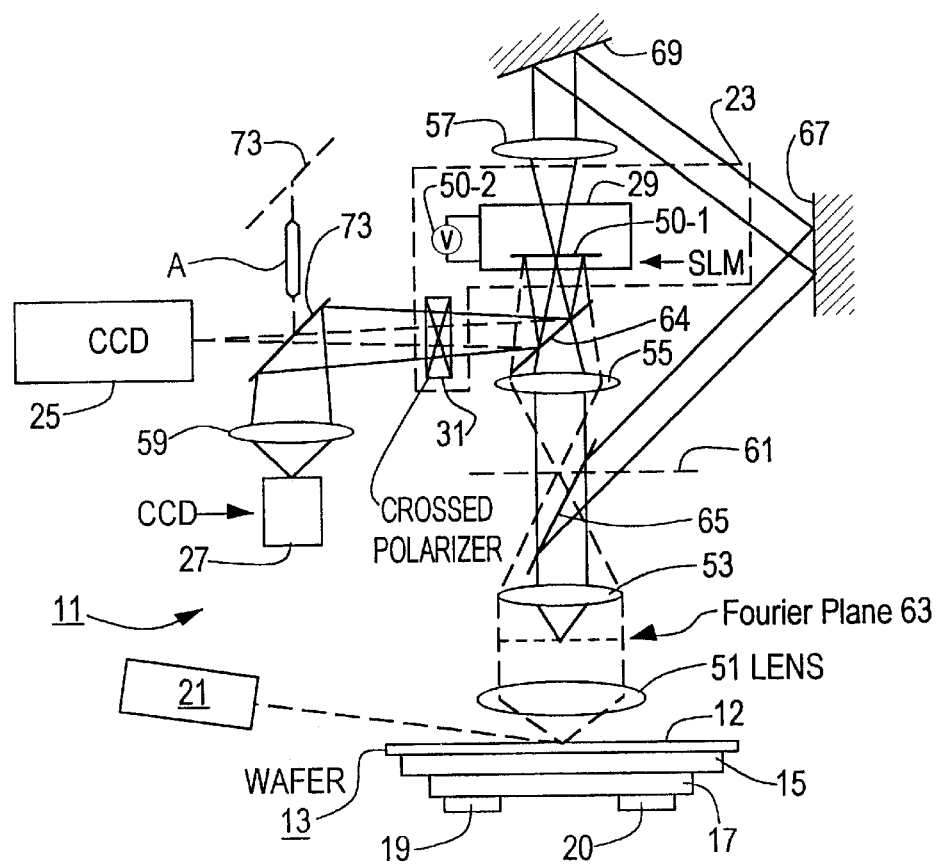
FIG. 1 is a schematic representation of an embodiment of an apparatus constructed according to the teaching of the present invention for detecting the presence of contaminant particles on surface of a semiconductor wafer having repetitive patterns.

Referring now to the drawings, there is illustrated in FIG. 1 an apparatus 11 for use in detecting the presence of particles on the front surface 12 surface of a semiconductor wafer 13 having repetitive patterns.

Apparatus 11 includes a holder 15 for holding wafer 13. Holder 15 is mounted on a stage 17 which is movable in two mutually perpendicular directions by a pair of motors 19 and 20, the particular details of the mechanical arrangement for moving stage 17 not being a part of this invention.

Apparatus 11 also includes a light source 21, a Fourier mask 23 which is self-programmable, a first light detector 25 and a second light detector 27.

Light source 21 generates a high intensity, plane polarized, coherent, monochromatic beam of light and may be, for example, a ND:YAG laser or a helium-neon laser.

Fourier mask 23 includes an optically addressable spatial light modulator (SLM) 29. Fourier mask 23 also includes a polarization discriminator in the form of a crossed polarizer 31.

Figure 2:
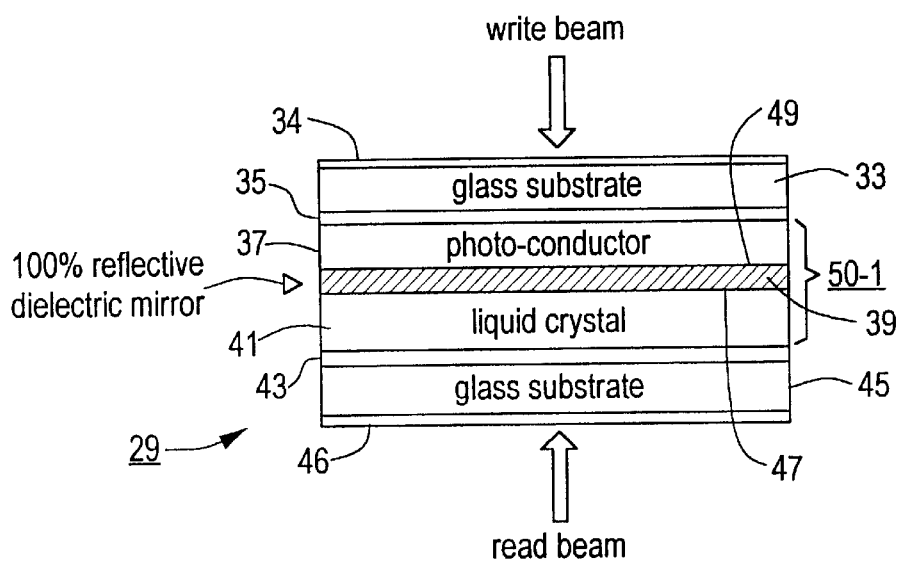
FIG. 2 is a detailed view of the spatial light modulator shown in FIG. 1.

Spatial light modulator 29, which is shown in detail in FIG. 2 includes a back plate of glass 33, an anti-reflection coating 34 on the back side of glass plate 33, a first transparent electrode 35 coated on the front side of glass plate 33, a photoconductive layer 37, such as amorphous silicon, in front of first transparent electrode 35, a 100% reflective dielectric mirror 39 in front of photoconductor 37, a liquid crystal 41 in front of dielectric mirror 39, a second transparent electrode 43 in front of liquid crystal 41, electrode 43 being coated on the back of a plate of glass 45 and an anti-reflection coating 46 on the front side of glass 45. Dielectric mirror 39 includes a front side 47 and a rear side 49. The thicknesses of layers 33, 37, 39, 41 and 45 may be as follows: layers 33 about 5 mm, layer 37 about 3 microns, layer 39 about 1 micron, layer 41 about 1 micron and layer 45 about 5 mm. For simplicity, layers 37, 39 and 41 on spatial light modulator 29 are shown in FIG. 1 as a single line 50-1. Electrodes 35 and 43 are on the order of about 1 micron thick.

SLM 29 is driven by a voltage source 50-2 which may be about 5 volts and which is connected to electrodes 35 and 43.

Optically addressable liquid crystal spatial light modulator 29 may be as an example ferroelectric liquid crystal spatial light modulator (FLC-SLM) model number X4601 made by Hamamatsu Photonics K.K., Central Research Laboratory, Hamakita City, Japan.

First light detector 25 is a high sensitivity video camera and second light detector 27 is a standard video camera. Each camera may be, for example, CCD type cameras.

Apparatus 11 also includes a first lens 51 which serves as an imaging lens, a second lens 53, a third lens 55, a fourth lens 57 and a fifth lens 59.

In the operation of apparatus 11, light from source 21 is directed onto front surface 12 of semiconductor wafer 13. Light source 21 is arranged so as to strike surface 12 at a grazing angle of incidence i.e. at an angle of between around 0 and 5 degrees. Light scattered upward from the area on surface 12 which is illuminated by the beam of light from source 21 is imaged by first lens 51 in combination with second lens 53 at intermediate image plane 61. As can be appreciated, the image formed at intermediate image plane 61 includes light scattered from any particles which may be present on the area of the surface illuminated and, in addition, light scattered from the pattern lines of the pattern on the area of the surface illuminated. A Fourier diffraction pattern of the scattered light is formed at the back focal plane 63 of lens 51.

The image of area of surface 12 illuminated by light source 21 which is formed at intermediate image plane 61 passes through a beamsplitter 64 and is reimaged by third lens 55 at first light detector 25 after being reflected off mirror 39 and being reflected off beamsplitter 64. In Fourier mask 23, light whose intensity is above a predetermined intensity level and corresponding to pattern lines on the surface of wafer 13 is blocked out.

Second lens 53 in combination with third lens 55 forms an image of the Fourier diffraction pattern from plane 63 on liquid crystal 41 in spatial light modulator 29 after passing through beamsplitter 64 and from there is reflected off mirror 39. A portion of the light passed by lens 53 corresponding to the Fourier diffraction pattern is reflected off of a beamsplitter 65 located between lens 53 and lens 55, then reflected off of a pair of mirrors 67 and 69 and then in combination with fourth lens 57 enters spatial light modulator 29 from the rear and is brought to focus at photoconductor 37. Thus, lens 53 and lens 55 are used to image the Fourier diffraction formed at plane 63 on liquid crystal 41 while lens 53 and 57 along with beamsplitter 65 and mirrors 67 and 69 are used to image the Fourier diffraction pattern formed at plane 63 onto photoconductor 37. The beam of light striking mirror 47 from liquid crystal 41 constitutes a "read" beam while the beam of light striking photoconductor 37 constitutes a "write" beam. The write beam and read beam are axially aligned on their corresponding sides of mirror 39 and are of the same size (magnitude). Thus there is point to point correspondence of the write and read beams at spatial light modulator 39.

In those areas (locations) where the intensity of the write beam is below a predetermined threshold level indicative of possible particle information, the polarization of the corresponding areas on the read beam on reflection from mirror 39 will be rotated 90 degrees. On the other hand, in those areas where the write beam is above the preselected threshold level indicative of background information, the polarization of corresponding areas on the read beam on reflection from mirror 39 will remain the same; i.e. will not be rotated.

Light reflected from mirror 39 is deflected off beamsplitter 64 and strikes crossed polarizer 31 which allows areas on the beam where the polarization has been rotated 90 degrees to pass through and blocks areas on the beam where the polarization has not been rotated. Light passed through polarizer 31 is then brought to focus on detector 25.

Thus, detector 25 records an image of light scattered from surface 12 whose intensity is below the predetermined threshold level and caused by particles and not scattered light whose intensity is above the threshold level and caused by pattern lines.

Apparatus 11 also includes a beamsplitting mirror 73 which is movable up and down as shown by arrows A. When mirror 73 is in the position shown, the Fourier diffraction pattern, after it is processed by Fourier mask 23, will be imaged by lens 59 onto detector 27 while the scattered light from surface 12 will be imaged onto detector 25 after it is processed by spatial light modulator 23. On the other hand, when mirror 73 is moved out the light path, as shown by the dotted lines only an image of the portion of wafer 11 illuminated, without the pattern lines, will be formed on camera 25 and no image will be formed on detector 27.

Wafer 13 is then moved translationally so that other areas on surface 12 may be examined, in a similar manner, one at a time.

As can be appreciated, Fourier mask 23 is self-programmable in that it automatically blocks out more intense portions of the light in the Fourier diffraction pattern.

Figure 3:
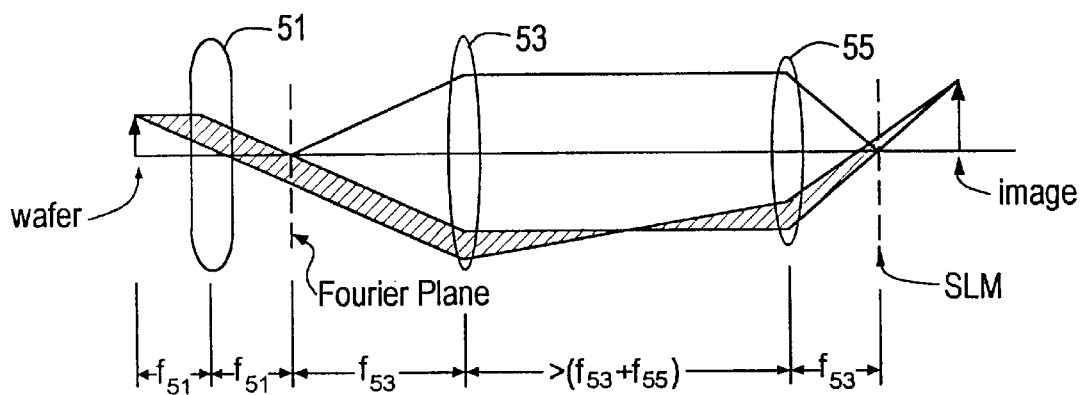
FIG. 3 is a ray trace of light from the semiconductor wafer to the detector in FIG. 1.

A ray trace of the light path from wafer 13 to detector 25 is shown in FIG. 3. Also shown in FIG. 3 is the spacing of some of the components.

Figure 4:
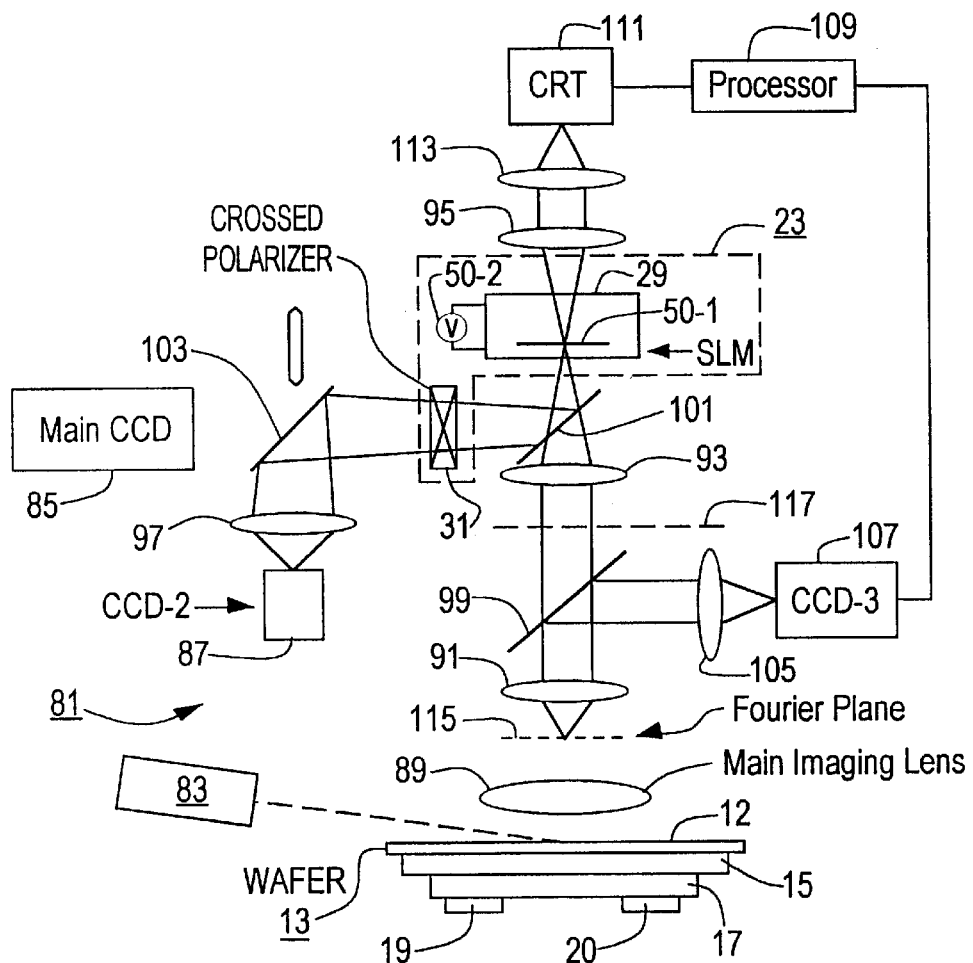
FIG. 4 is a schematic representation of another embodiment of the invention.

Referring now to FIG. 4 there is shown another embodiment of an apparatus constructed according to this invention, the apparatus being identified by reference numeral 81.

Apparatus 81 differs from apparatus 11 in that a portion of the Fourier diffraction pattern formed in the Fourier plane is not used directly as the write beam, as in apparatus 11, but, rather, is converted into electrical signals which are processed and then converted back to a video image which is then used as the write beam.

Apparatus 81 includes a light source 83, a first light detector 85, a second light detector 87, a first lens 89, a second lens 91, a third lens 93, a fourth lens 95, a fifth lens 97, a first beamsplitter 99, a second beamsplitter 101 and a third beamsplitter 103 corresponding structurally and functionally, respectively to light source 21, light detector 25, light detector 27, first lens 51, second lens 53, third lens 55, fourth lens 57, fifth lens 59 beamsplitters 65 and 71 and movable mirror 73, respectively, in apparatus 11.

Apparatus 81 also includes a self-programmable Fourier mask 23.

However, instead of mirrors 67 and 69, apparatus 81 includes a sixth lens 105, a third light detector 107, a processor 109, a CRT 111 and a seventh lens 113. Detector 107 is identical in construction to detector 87.

Lens 105 in combination with lens 91 images the Fourier diffraction pattern formed in Fourier plane 115 of lens 89 into light detector 107 where the image is converted into a stream of digital electrical signals. The stream of digital electrical signals are processed in processor 109, as maybe desired. The processing may include raising the overall gain of the image or blocking out selected areas. The output of processor 109 is fed into CRT 111 which converts the digital electrical signals into a video image. The video image from CRT 111 is collected by lens 113 and then reimaged by lens 95 through glass 33 onto photoconductor 37 in spatial light modulator 29. At the same time, lens 91 in combination with lens 93 images the Fourier diffraction pattern through glass layer 45, transparent electrode 43 and liquid crystal 41 onto mirror 39. Lens 89 in combination with lens 91 forms an image of the area illuminated by light source 83 at image plane 117. The image formed at image plane 117 is then collected by lens 93 and passed through Fourier mask 85, using beamsplitter 101. The filtered image is then brought to focus at detector 85. The diffraction pattern at Fourier plane 115 is imaged at detector 87 after it passes through mask 23.

Figure 5:
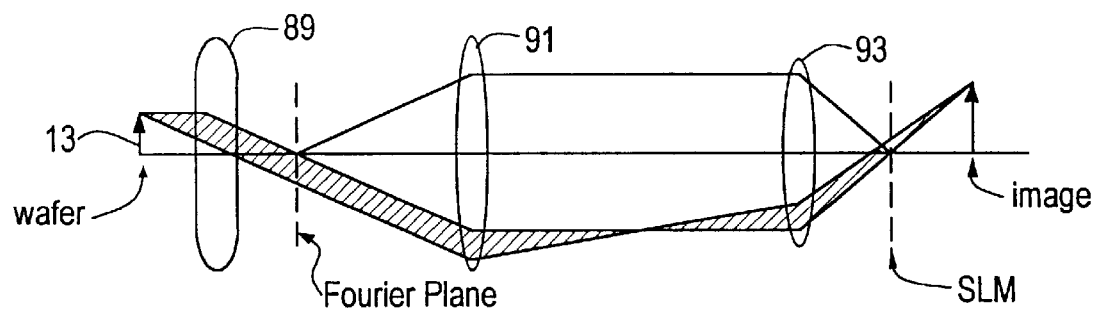
FIG. 5 is a ray trace of light from the semiconductor wafer to the detector in the FIG. 4 embodiment of the invention.

A ray trace of light from wafer 13 to camera 91 is shown in FIG. 5.

As can be appreciated, in apparatus 11 and apparatus 81, the read and write beams are separate beams and must be mutually aligned.

Figure 6:
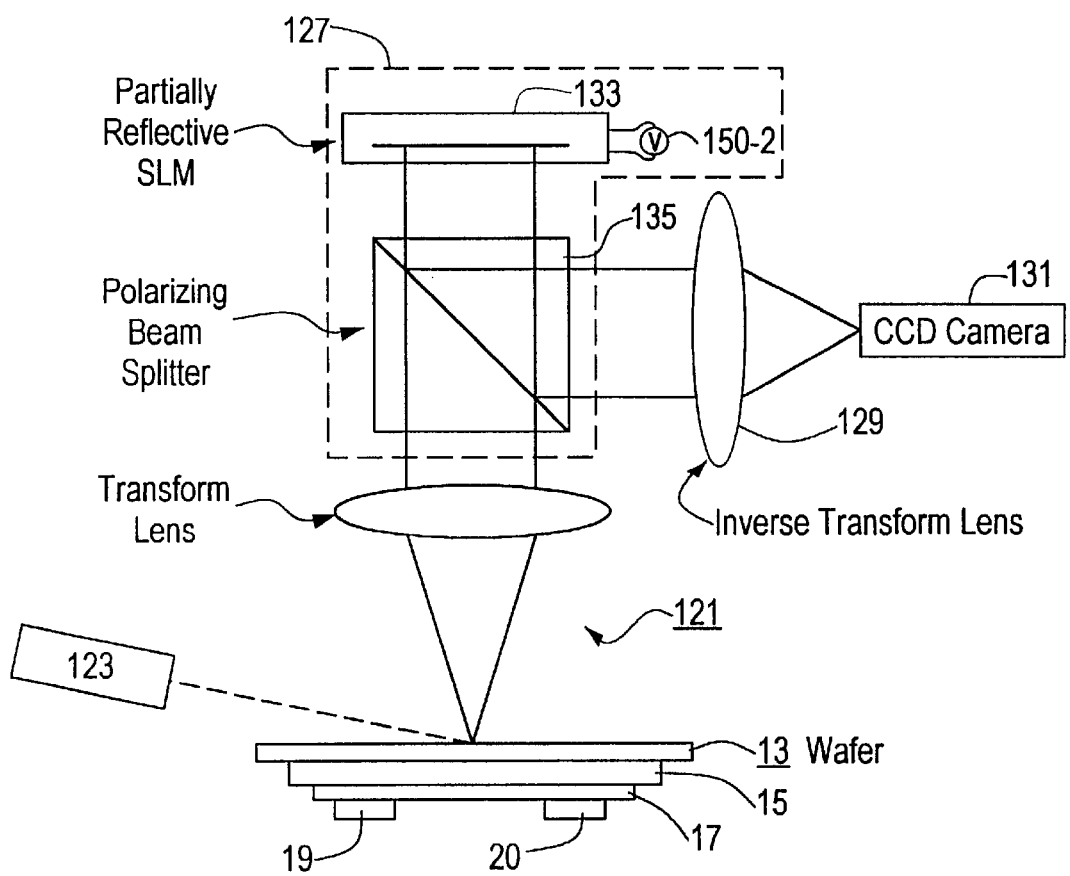
FIG. 6 is a schematic representation of another embodiment of the invention.

Referring now to FIG. 6, there is shown another embodiment of the invention, the apparatus being identified by reference numeral 121. In this embodiment, the same beam is used for reading and writing, i.e. is not split up into two parts as in apparatus 11 and apparatus 81, thereby eliminating the alignment task.

Apparatus 121 includes a light source 123, a transform lens 125, a self-programmable Fourier mask 127, an inverse transform lens 129 and a light detector 131. Fourier mask 127 includes a partially reflective spatial light modulator 133 and a polarization discriminator which is in the form of a polarizing beamsplitter 135. Apparatus 121 also includes a holder 15 for holding a wafer 13 to be tested and a stage 17 on which holder 15 is mounted. Stage 17 is movable in two mutually perpendicular directions by a pair of motors 19 and 20. Light source 123 and camera 131 correspond structurally and functionally to lightsource 21 and detector 25, respectively. SLM 133 is a partially reflective spatial light modulator in that it contains a partially, as opposed to fully, reflective mirror as will hereinafter be described.

Figure 7:
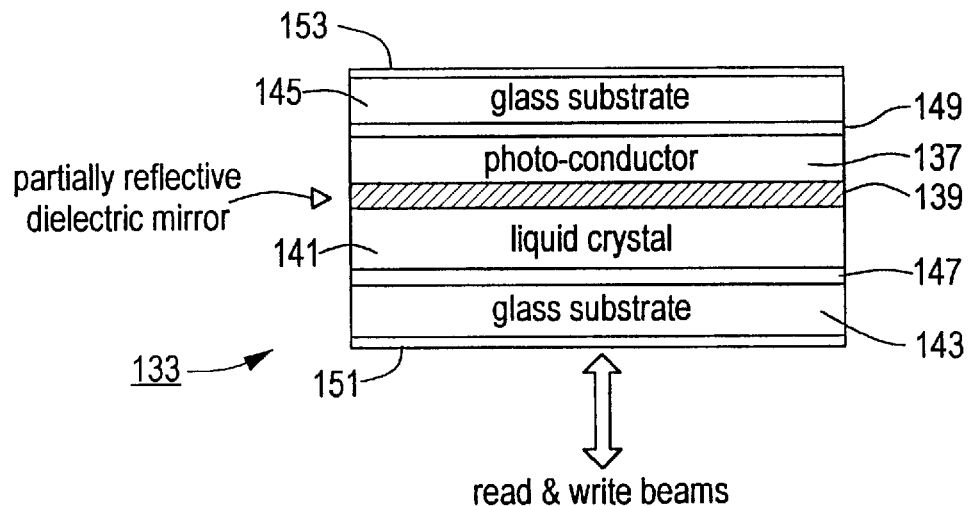
FIG. 7 is a detailed view of the spatial light modulator shown in FIG. 6.

Partially reflective spatial light modulator 133, which is shown in detail in FIG. 7, is optically addressable and includes an amorphous silicon photoconductive layer 137, a partially reflective dielectric mirror 139 and a ferroelectric liquid crystal 141 disposed between a pair of glass plates 143 and 145 which are coated on their inner surfaces with transparent electrodes 147 and 149 and on their outer surfaces with anti-reflection coating 151 and 153. A voltage source 150-2 identical to voltage source 50-2 is coupled to electrodes 147 and 149.

Polarizing beam splitter 135 transmits light that is polarized parallel to its plane of incidence and reflects light that is polarized orthogonal to that plane. Transform lens 125 and inverse transform lens 129 are used at infinite conjugates so that polarized beam splitter 135 can be used with collimated light, thereby minimizing any angle-induced performance degradation. SLM 133 is disposed at the back focal plane of transform lens 129.

In the operation of apparatus 121, light from source 123 is directed onto front surface of wafer 13 at grazing angle of incidence. Light scattered upward from wafer 13 is collected by transform lens 125 passes through polarizing beam splitter 135 and strikes spatial light modulator 133. The portion of the light beam that is transmitted through partially reflective dielectric mirror 139 serves as the write beam and strikes photoconductor 137. The portion of the light beam that is reflected by partially reflective dielectric mirror 133 serves as the read beam. As in the case of apparatus 11 and apparatus 81, in areas where the light in the write beam is above a predetermined threshold level, the polarization of the reflected beam will remain the same, while in areas where the light in the write beam is below the predetermined threshold level the polarization of the reflected beam will be rotated 90 degrees.

Light reflected from SLM 133 strikes polarizing beam splitter 135.

The light whose polarization has been rotated 90 degrees is reflected by polarizing beam splitter 135 and then imaged by inverse transform lens 129 onto detector 131. The light whose polarization has not been rotated is transmitted through polarizing beam splitter 135.

Figure 8:
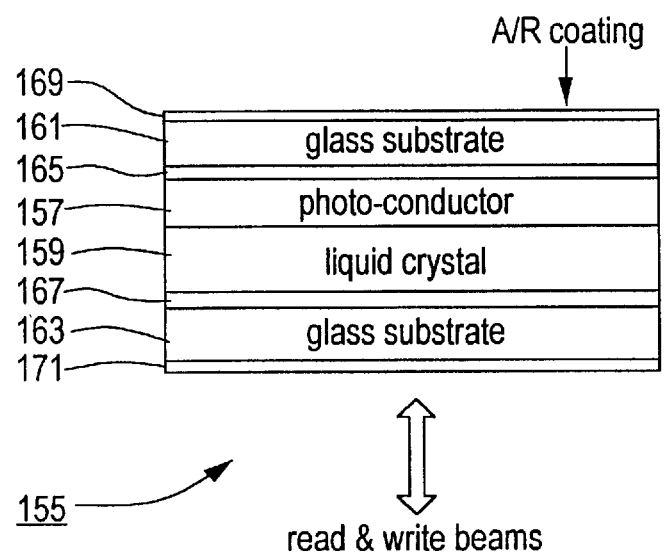
FIG. 8 is a detailed view of a modification of the spatial light modulator shown in FIG. 6.

Referring now to FIG. 8, there is shown another version of a partially reflective spatial light modulator (SLM), the version being identified by reference numeral 155. SLM 155 is optically addressable and includes an amorphous silicon photoconductive layer 157 and a ferroelectric liquid crystal 159 disposed between a pair of glass plates 161 and 163 coated on the inner surfaces with transparent electrodes 165 and 167 and on their outer surfaces with anti-reflection coatings 169 and 171. As can be seen, in SLM 155 there is no dielectric film; instead, partial reflectance is achieved by relying on the Fresnel reflection/transmission at the liquid crystal-photoconductor interface. SLM 155 may be used in place of SLM 133 in apparatus 121.

Figure 9:
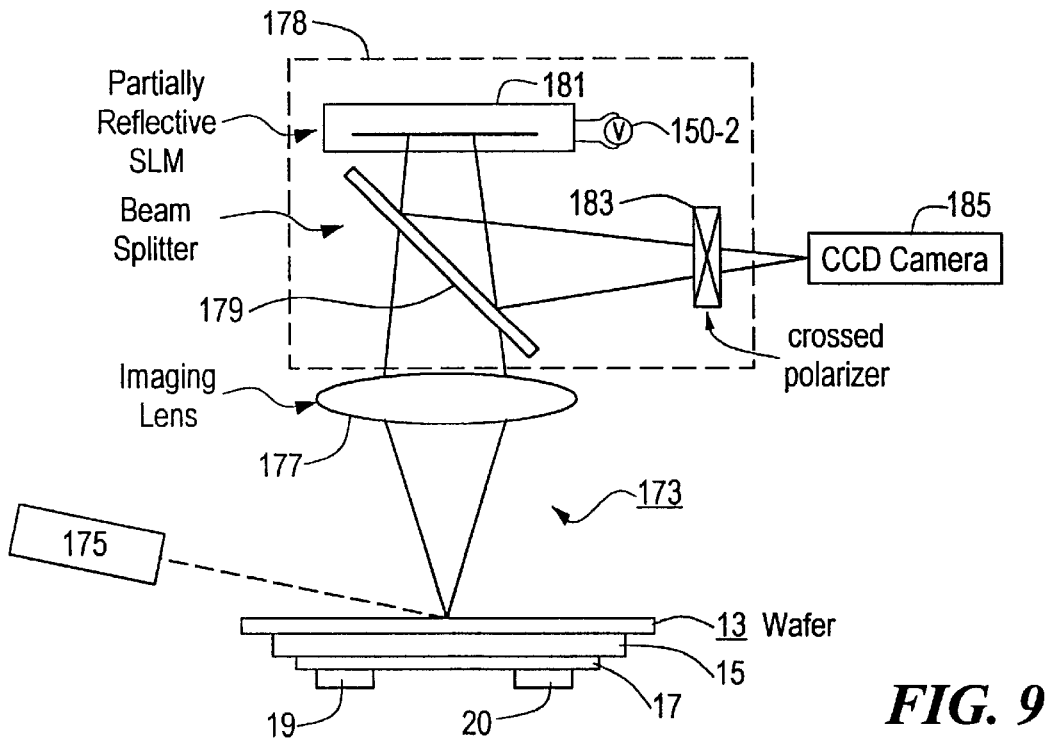
FIG. 9 is a schematic representation of another embodiment of the invention.

Referring now to FIG. 9, there is shown another embodiment of the invention, identified by reference numeral 173. Apparatus 173 differs from apparatus 121 in that it includes an imaging lens instead of a transform lens and an inverse transform lens and, in addition, includes a self-programmable Fourier mask comprising a beam splitter, a partially reflective SLM and a crossed polarizer rather than a partially reflective SLM and a polarizing beam splitter.

As can be seen, apparatus 173 includes a light source 175 identical to light source 21, an imaging lens 177, a Fourier mask 178 comprising a 50:50 plate, a beam splitter 179, a partially reflective SLM 181 and a polarization discriminator in the form of a crossed polarizer 183. Apparatus 173 further includes a detector 185. Apparatus 173 also includes a holder 15, a stage 17 and a pair of motors 19 and 20. SLM 155 may be used, if desired, in place of SLM 181. SLM 181 is disposed at the back focal plane of imaging lens 177.

In the operation of apparatus 173, light scattered from wafer 13 and collected by imaging lens 177 passes through beam splitter 179 and strikes SLM 181. Light reflected from SLM 181 is reflected off beam splitter 179 and strikes crossed polarizer 183. Light whose polarization has been rotated 90 degrees passes through crossed polarizer 183 and is imaged on detector 185 while light whose polarization has not been changed is blocked by crossed polarizer 183.

Figure 10:
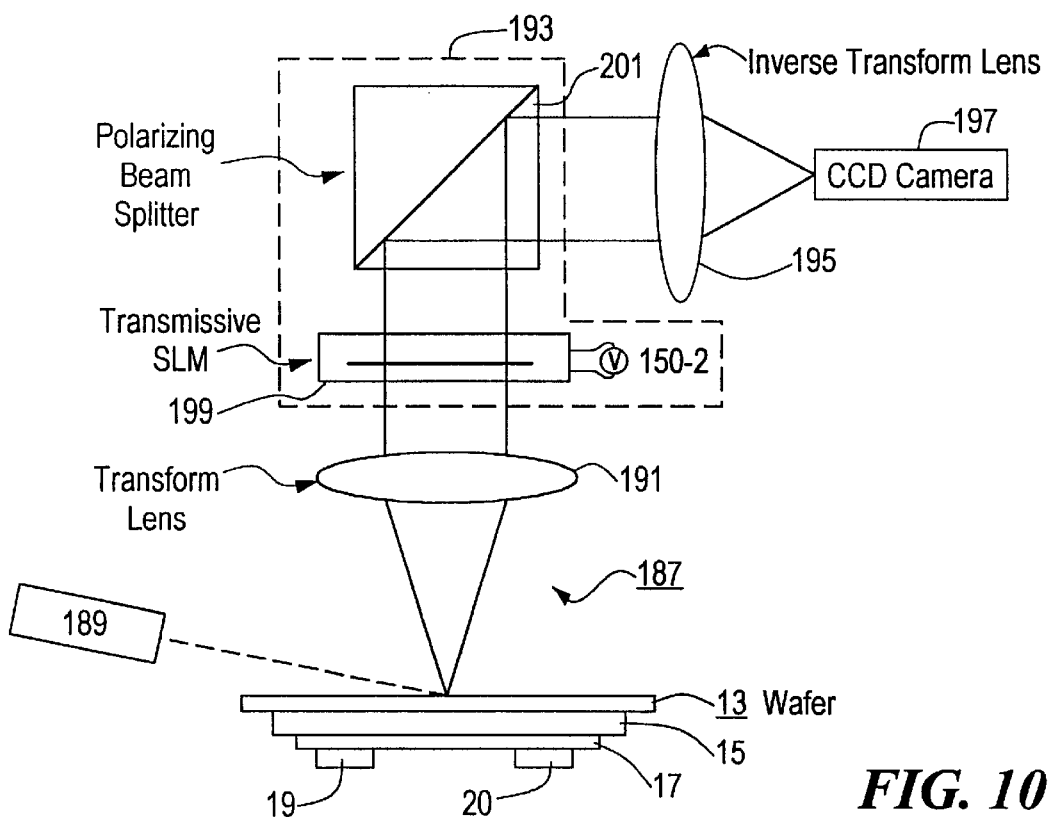
FIG. 10 is a detailed view of another embodiment of the invention.

Referring now to FIG. 10, there is shown another embodiment of the invention identified by reference numeral 187.

Apparatus 187 includes a light source 189, a transform lens 191, a self-programmable Fourier mask 193, an inverse transform lens 195 and a light detector 197. Fourier mask 193 includes a transmissive spatial light modulator 199 and a polarization discriminator which is in the form of a polarizing beamsplitter 201. Apparatus 187 also includes a holder 15 for holding a wafer 13 to be tested and a stage 17 on which holder 15 is mounted. Stage 17 is movable in two mutually perpendicular directions by a pair of motors 19 and 20. Light source 189 and detector 197 correspond structurally and functionally to light source 21 and detector 25, respectively.

Figure 11:
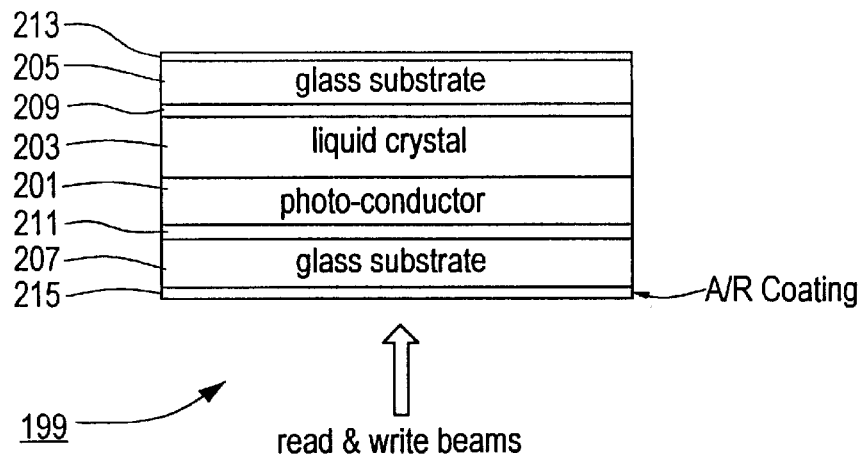
FIG. 11 is a detailed view of another embodiment of the invention.

Transmissive spatial light modulator 199, which is located at the back focal plane of transform lens 191 and which is shown in detail in FIG. 11, is optically addressable and includes an amorphous silicon photoconductive layer 201 and a ferroelectric liquid crystal 203 disposed between a pair of glass plates 205 and 207 which are coated on their inner surfaces with transparent electrodes 209 and 211 and on their outer surfaces with anti-reflection coatings 213 and 215. SLM 199 is driven by voltage source 150-2 which is coupled to electrodes 209 and 211.

Polarizing beam splitter 201 transmits light that is parallel to its plane of incidence and reflects light that is orthogonal to that plane. SLM 199 rotates by 90 degrees the polarization of light whose intensity is below a predetermined threshold level and leaves unchanged the polarization of light incident therein whose intensity is above that predetermined threshold level. Transform lens 191 and inverse transform lens 195 are used at infinite conjugates so that polarized beam splitter 201 can be used with collimated light, thereby minimizing any angle-induced performance degradation. SLM 199 is disposed at the back focal plane of transform lens 191.

In the operation of apparatus 187, light from source 189 is directed onto front surface of wafer 13. Light scattered from wafer 13 is collected by transform lens 191 and passes through SLM 199 and strikes polarizing beam splitter 201. Light whose polarization has been rotated 90 degrees is reflected by polarization beam splitter and then brought to focus on detector 197 by inverse transform lens 195.

Figure 12:
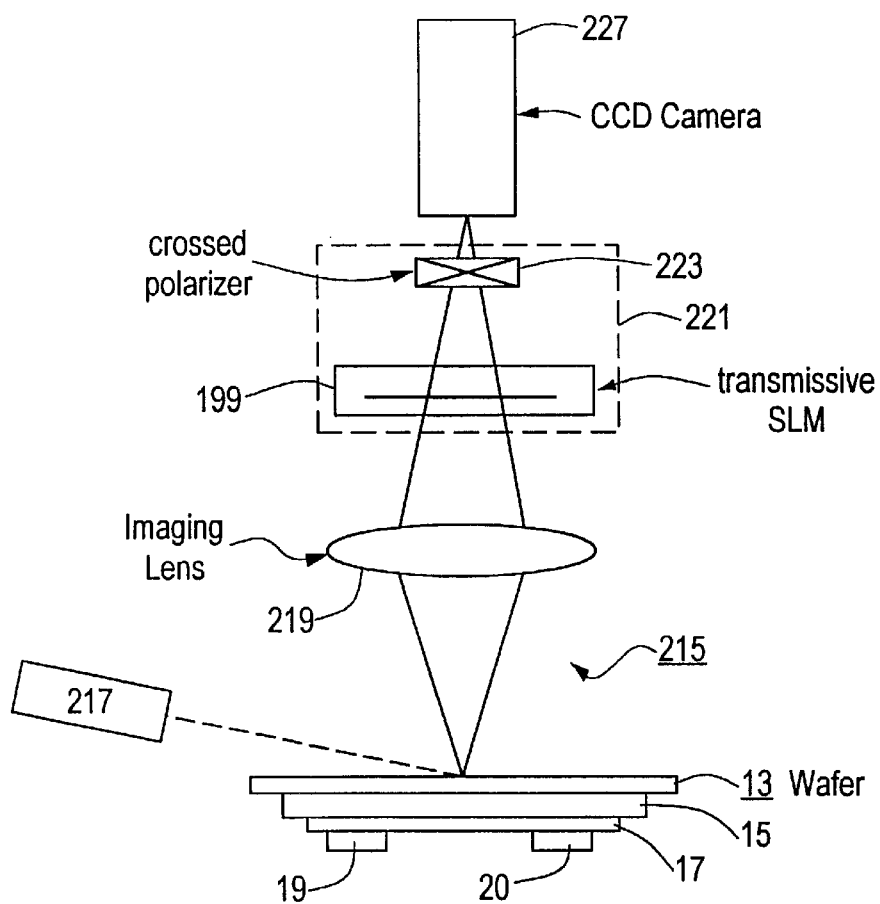
FIG. 12 is a detailed view of another embodiment of the invention.

Referring now to FIG. 12, there is shown another embodiment of the invention, the embodiment being identified by reference numeral 215. Apparatus 215 differs from apparatus 187 in that it includes an imaging lens instead of a transform lens and inverse transform lens and, in addition, includes a self-programmable Fourier mask comprising a transmissive SLM and a crossed polarizer rather than a transmissive SLM and a polarizing beam splitter.

Accordingly, apparatus 215 includes a light source 217, an imaging lens 219, a Fourier mask 221 comprising a transmissive, optically addressable SLM 199. Apparatus 215 further includes a polarization discriminator in the form of a crossed polarizer 223. Apparatus also includes a detector 227, a holder 15, a stage 17, and a pair of motors 19 and 20. SLM 199 is disposed at the back focal plane of imaging lens 219.

In the operation of apparatus 215, light scattered from wafer 13 and collected by imaging lens 219 passes through SLM 199 and strikes crossed polarizer 223. Light whose intensity is below a predetermined threshold level has its polarization rotated 90 degrees while the polarization of light whose intensity is above that remains unchanged. Light passed by crossed polarizer 223 is imaged onto detector 227.

The embodiments of the present invention recited herein are intended to be merely exemplary and those skilled in the art will be able to make numerous variations and modifications to it without departing from the spirit of the present invention. For example, an array of photodiodes can be used in place of any or each one of the cameras. Also, cameras 25 and 85 could be replaced by non-imaging detectors, such as a photomultiplier tube if an image of the area illuminated is not desired. All such variations and modifications are intended to be within the scope of the present invention as defined by the claims appended hereto.

What is claimed is:

1. Apparatus for detecting particles on a surface of a semiconductor wafer, said surface having repetitive patterns, the apparatus comprising:
   a. means for illuminating an area on said surface with a beam of polarized light,
   b. optical means for collecting light scattered from said area, said optical means forming a Fourier diffraction pattern of light scattered from said area illuminated,
   c. a Fourier mask for blocking light in said Fourier diffraction pattern where the intensity is above a predetermined level indicative of background information and leaving in areas where the intensity is below said predetermined level indicative of particle information, the Fourier mask including a spatial light modulator which is optically addressable and a polarization discriminator, and
   d. a detector for detecting light collected by said optical means and not blocked by said Fourier mask.

2. The apparatus of claim 1, wherein said spatial light modulator is fully reflective.

3. The apparatus of claim 2, wherein said polarization discriminator is a crossed polarizer.

4. The apparatus of claim 3, wherein said optical means comprises an imaging lens.

5. The apparatus of claim 4, wherein said spatial light modulator includes a 100% reflective mirror.

6. The apparatus of claim 5, wherein said 100% reflective mirror is a dielectric mirror.

7. The apparatus of claim 1, wherein said optically addressable spatial light modulator is partially reflective.

8. The apparatus of claim 7, wherein said polarization discriminator is a polarizing beamsplitter.

9. The apparatus of claim 8, wherein said optical means comprises a transform lens and said apparatus further includes an inverse transform lens.

10. The apparatus of claim 8, wherein said optical means comprises an imaging lens.

11. The apparatus of claim 7, wherein said polarization discrimination is a crossed polarizer.

12. The apparatus of claim 11, wherein said optical means comprises a transform lens and said apparatus further includes an inverse transform lens.

13. The apparatus of claim 1, wherein said optically addressable spatial light modulator is transmissive.

14. The apparatus of claim 13, wherein said polarization discrimination is a polarizing beamsplitter.

15. The apparatus of claim 14, wherein said optical means comprises a transform lens and said apparatus further includes an inverse transform lens.

16. The apparatus of claim 13, wherein said polarization discrimination is a crossed polarizer.

17. The apparatus of claim 16, wherein said optical means is an imaging lens.

18. A method for detecting particles on a surface of a semiconductor wafer, said surface having repetitive patterns, the method comprising:
   a. illuminating an area on said surface with a beam of polarized light,
   b. collecting light scattered from said area and for forming a Fourier diffraction pattern of said light collected,
   c. removing from said Fourier diffraction pattern light whose intensity is above a predetermined level indicative of background information and leaving in areas whose intensity is below said threshold level indicative of particle information using a spatial light modulator which is optically addressable and a polarization discrimination, and
   d. recording an image of light collected by said optical means and not removed by said Fourier mask.

19. Apparatus for detecting particles on a surface of a semiconductor wafer, said surface having repetitive patterns, the apparatus comprising:
   a. means for illuminating an area on said surface with a beam of polarized light,
   b. optical means for collecting light scattered from said area, said optical means forming a Fourier diffraction pattern of light scattered from said area illuminated,
   c. a Fourier mask for blocking light in said Fourier diffraction pattern where the intensity is above a predetermined level indicative of background information and leaving in areas where the intensity is below said predetermined level indicative of particle information, the Fourier mask including an optically addressable spatial light modulator and a polarization discriminator, said optically addressable spatial light modulator including a photoconductive layer and a liquid crystal, and
   d. a detector for detecting light collected by said optical means and not blocked by said Fourier mask.

20. The apparatus of claim 19 wherein said Fourier mask is self-programmable.

21. Apparatus for detecting particles on a surface of a semiconductor wafer, said surface having repetitive patterns, the apparatus comprising:
   a. means for illuminating an area on said surface with a beam of polarized light,
   b. optical means for collecting light scattered from said area, said optical means forming a Fourier diffraction pattern of light scattered from said area illuminated,
   c. a Fourier mask for blocking light in said Fourier diffraction pattern where the intensity is above a predetermined level indicative of background information and leaving in areas where the intensity is below said predetermined level indicative of particle information, the Fourier mask including a spatial light modulator and a polarization discriminator,
   d. said spatial light modulator being constructed to receive a read and write beam, said scattered light collected by said optical means being used to provide said read beam and said write beam, and
   e. a detector for detecting light collected by said optical means and not blocked by said Fourier mask.

22. Apparatus for detecting particles on a surface of a semiconductor wafer, said surface having repetitive patterns, the apparatus comprising:

a. means for illuminating an area on said surface with a beam of polarized light,
b. optical means for collecting light scattered from said area, said optical means forming a Fourier diffraction pattern of light scattered from said area illuminated,
c. a Fourier mask for blocking light in said Fourier diffraction pattern where the intensity is above a predetermined level indicative of background information and leaving in areas where the intensity is below said predetermined level indicative of particle information, the Fourier mask including a spatial light modulator and a polarization discriminator,
d. said spatial light modulator being addressed using light collected by said optical means, and
e. a detector for detecting light collected by said optical means and not blocked by said Fourier mask.

* * * * *